United States Patent
Habermann et al.

(10) Patent No.: US 7,202,059 B2
(45) Date of Patent: Apr. 10, 2007

(54) FUSION PROTEINS CAPABLE OF BEING SECRETED INTO A FERMENTATION MEDIUM

(75) Inventors: Paul Habermann, Eppstein (DE); Johann Ertl, Eppstein (DE)

(73) Assignees: Sanofi-Aventis Deutschland GmbH, Frankfurt (DE); Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/076,634

(22) Filed: Feb. 19, 2002

(65) Prior Publication Data

US 2003/0044906 A1 Mar. 6, 2003

Related U.S. Application Data

(60) Provisional application No. 60/270,593, filed on Feb. 23, 2001.

(30) Foreign Application Priority Data

Feb. 20, 2001 (DE) ................. 101 08 212

(51) Int. Cl.
C12P 21/04 (2006.01)
C07H 21/04 (2006.01)
(52) U.S. Cl. .................. 435/69.7; 435/70.1; 435/71.1; 435/71.2; 435/325; 435/252.31; 435/252.33; 435/252.35; 536/23.4
(58) Field of Classification Search ............... 435/69.7, 435/70.1, 71.1, 71.2, 320.1, 252.3, 252.31, 435/252.33, 252.35; 536/23.4
See application file for complete search history.

(56) References Cited

U.S. PATENT DOCUMENTS

| | | | |
|---|---|---|---|
| 5,316,947 A | 5/1994 | Crause et al. | |
| 5,677,172 A | 10/1997 | Makarow | |
| 5,705,355 A | 1/1998 | Tolstoshev et al. | |
| 5,824,505 A | 10/1998 | Tolstoshev et al. | |
| 6,103,502 A | 8/2000 | Möller et al. | |

FOREIGN PATENT DOCUMENTS

| | | |
|---|---|---|
| AU | 726264 | 2/2001 |
| EP | 0 195 691 B1 | 9/1986 |
| EP | 0 214 826 B1 | 3/1987 |
| EP | 0 324 712 B1 | 7/1989 |
| EP | 0 347 781 B1 | 12/1989 |
| EP | 0 375 437 B1 | 6/1990 |
| EP | 0 419 504 B1 | 4/1991 |
| EP | 0 448 093 B1 | 9/1991 |
| EP | 0 468 539 B1 | 1/1992 |
| EP | 0 489 780 B1 | 6/1992 |
| EP | 0 511 393 A1 | 11/1992 |
| EP | 0 200 655 B1 | 4/1995 |
| EP | 0 678 522 B1 | 10/1995 |
| WO | WO 91/09125 | 6/1991 |
| WO | WO 92/00321 | 1/1992 |
| WO | WO 01/21662 A1 | 3/2001 |
| WO | WO 02/04486 | 1/2002 |
| WO | WO 02/04486 A2 | 1/2002 |

OTHER PUBLICATIONS

Online Medical Dictionary—definition of signal sequence http://cancerweb.nci.ac.uk.*

Bio Critical Synergy: The Biotechnology Industy and Intellectual Property Organizatin, Presentations Oct. 17, 1994 pp. 75-107.*

Merriam-Webster Online Dictionary http://www.m-w.com/cgi-bin definition of fermentation and Supernatant.*

Dé et al., "Channel-forming properties and structural homology of major outer membrane proteins from *Pseudomonas fluorescens* MFO and OE 28.3," *FEMS Microbiology Letters*, 127, 267-272, 1995.

Fürste et al, "Molecular cloning of the plasmid RP4 primase region in a multi-host-range *tacP* expression vector," *Gene*, 48(1), 119-131, 1986.

Griessbach et al., "Assay of Hirudin in Plasma Using a Chromogenic Thrombin Substrate," *Thrombosis Research*, 37, 347-350, 1985.

Price et al., "Expression, purification and characterization of recombinant murine granulocyte-machrophage colony-stimulating factor and bovine interleukin-2 from yeast," *Gene*, 55(2-3), 287-293, 1987.

Rioux et al., "Genes on the 90-Kilobase Plasmid of *Salmonella typhimurium* Confer Low-Affinity Cobalamin Transport: Relationship to Fimbria Biosynthesis Genes," *Journal of Bacteriology*, 172(11), 6217-6222, 1990.

Rosenfeld et al., Production and Purification of Recombinant Hirudin Expressed in the Methylotrophic Yeast *Pichia pastoris*, *Protein Expression and Purification*, 8(4), 476-482, 1996.

Shuttleworth et al., "Sequence of the gene for alkaline phosphatase from *Escherichia coli* JM83," *Nucleic Acids Research*, 14(21), 8689, 1986.

(Continued)

Primary Examiner—Patricia A. Duffy
(74) Attorney, Agent, or Firm—George S. Jones

(57) ABSTRACT

Fusion protein including a fusion part and a protein of interest, the combination of the two proteins leading to the fusion protein being secreted into a supernatant of a bacterial host with the protein of interest being present in its correct three-dimensional structure. Nucleic acid including a sequence coding for a fusion protein, the sequence including: —F—$As_m$—$R_n$—Y—, where F is a nucleic acid sequence coding for an amino acid sequence which allows secretion of a protein encoded by Y into a fermentation medium, As is a chemical bond or a nucleic acid sequence comprising a codon, m is an integer from 0–10, R is a chemical bond or an arginine codon, n is 0 or 1, and Y is a nucleic acid sequence coding for a protein of interest. Processes therefor.

18 Claims, No Drawings

OTHER PUBLICATIONS

Wetekam et al., "The nucleotide sequence of cDNA coding for preproinsulin from the primate *Macaca fascicularis*," *Gene*, 19(2), 179-183, 1982.

Weydemann et al., "High-level secretion of hirudin by *Hansenula polymorpha*—authentic processing of three different preprohirudins," *Applied Microbiology and Biotechnology*, 44(3-4), 377-385, 1995.

Winter et al., "Increased Production of Human Proinsulin in the Periplasmic Space of *Escherichia Coli* by Fusion to DsbA," *Journal of Biotechnology*, 84, 175-185 (2000).

Thim et al., "Secretion and Processing of Insulin Precursors in Yeast," *Proc. Natl. Acad. Sci.*, 83: 6766-6770 (1986).

\* cited by examiner

FUSION PROTEINS CAPABLE OF BEING SECRETED INTO A FERMENTATION MEDIUM

CROSS-REFERENCE TO RELATED APPLICATIONS

This application claims the priority under 35 U.S.C. § 119(e) of U.S. Provisional Application No. 60/270,593, filed Feb. 23, 2001, the disclosure of which is expressly incorporated by reference herein in its entirety, and also claims priority under 35 U.S.C. § 119 of German Application No. 101 08 212.6, filed Feb. 20, 2001, the disclosure of which is expressly incorporated by reference herein in its entirety.

DESCRIPTION OF THE INVENTION

The invention relates to fusion proteins comprising a fusion part and a protein of interest. The combination of the two proteins results in a fusion protein that is secreted into the supernatant of a bacterial host with the protein of interest being present in its correct three-dimensional structure. The gene sequence for the fusion protein may be part of an expression cassette that allows expression in a bacterial host. The invention may relate to a process for the fermentation, expression and work-up of such a fusion protein using the expression cassette, to a plasmid containing the expression cassette, to a bacterial host cell containing the expression cassette integrated into the chromosome and/or as a replicon, for example as a plasmid, to said fusion protein with hirudin or a derivative thereof as the fusion part, to a process for producing insulin or an insulin derivative and to the use of the expression cassette in the processes for preparing a fusion protein from hirudin or derivatives thereof and for producing insulin or an insulin derivative.

The development of optimized processes for producing pharmaceuticals on the basis of recombinant proteins represents a task that typically has at least two considerations. First, a process ought to be as cost-effective as possible. Second, the product ought to be of the highest purity.

In this regard, the choice of expression system determines the course of the particular production process. The development of novel protein-chemical techniques and the wide variety of biochemical possibilities and new combinations of known techniques always make improvements of existing processes possible.

The properties of a desired protein determine the choice of the host cell system used for its synthesis. Bacteria such as *Escherichia coli* represent a system for rapidly producing proteins with crude yields of several grams in inexpensive media. The system comes in useful especially for proteins which need not be modified and which can be renatured in vitro to their biologically active form. For proteins which are needed in high quantities, such as insulin for example, expression rates leading to intracellular accumulation of the protein in the form of inclusion bodies are desired. After cell lysis, the protein is dissolved and then, in further process steps, folded. However, the process of folding is not quantitative. Reasons for this may be irreversible damage during inclusion body formation, corresponding damage during cell lysis and errors during folding. "Wrongly" folded or modified molecules then have to be removed in further separation steps. This has an adverse effect on production costs. In addition, traces of said molecules also appear in the final product. Since pharmaceuticals are subject to high criteria of purity, an appropriately careful and cost-intensive purification is necessary. Owing to the favorable cost/crude yield ratio, processes allowing export by *E. coli* of the protein of interest in correctly folded form into the culture medium would be desirable. However, this has been successful only in exceptional cases up until now.

International patent application PCT/EP00/08537 describes such an exception. Synthesis and export of the hirudin derivative lepirudin, the active ingredient of the pharmaceutical REFLUDAN™, by *E. coli* in gram quantities was successful when using specific signal sequences for exporting. German Application No. 100 33 195.2 (unpublished) describes a bifunctional protein composed of hirudin and hirudin derivatives and of factor Xa inhibitor from ticks and derivatives thereof. Said protein can likewise be synthesized and exported by *E. coli* with high yields. In addition, it was then surprisingly found that hirudin is exported with high yields not only as a fusion protein with TAP but also as part of a fusion protein with polypeptides such as proinsulin derivatives, that it is biologically active and that surprisingly a fusion partner such as proinsulin is present in the correct three-dimensional structure. This unexpected result leads to the possibility of more cost-effective production of, for example, insulin by bacterial host/vector systems, since the step of in vitro refolding after intracellular expression, which is associated with losses in yield which are not negligible, can be dispensed with and in this way a simpler protein purification process results. Another advantage is that chaotropic aids added to dissolve the fusion protein in traditional processes for the production of insulin in *E. coli* are not required. Ecologically, this leads to less environmental pollution by avoiding the corresponding waste.

Leeches of the *Hirudo* type have developed, for example, various isoforms of the thrombin inhibitor hirudin. Hirudin has been optimized for pharmaceutical requirements by artificial variation of the molecule, for example exchange of the N-terminal amino acid (e.g., EP-A 0 324 712).

The invention includes the use of hirudin and hirudin variants for the formation of fusion proteins, for example with simian proinsulin or derivatives thereof. Particular aspects of the invention use one of the natural hirudin isoforms (the natural isoforms together are denoted "hirudin"). Natural isoforms are, for example, Val-Val-hirudin or Ile-Thr-hirudin. Other aspects of the invention use a variant of a natural hirudin isoform. A hirudin variant is derived from a natural hirudin isoform but contains, for example, additional amino acids and/or amino acid deletions and/or amino acid exchanges compared with the natural isoform. A hirudin variant may contain alternating peptide segments of natural hirudin isoforms and new amino acids. Hirudin variants are known and are described, for example, in DE 3 430 556. Hirudin variants are commercially available in the form of proteins (CALBIOCHEM™ Biochemicals, Cat. No. 377-853, -950-960). The hirudin variant sequences are at least 40% homologous to lepirudin, such that 40% of the total amount of the 65 amino acids known from lepirudin should be found within the variant. The hirudin variant sequences may be even more homologous, such as at least about 60%, or at least about 80%, homologous to hirudin. The % homology is calculated by the Compare Program which is available from the WISCONSIN PACKAGE™ distributed by the Genetics Computer Group; 575 Science Drive; Madison, Wis.

Insulin is a polypeptide of 51 amino acids which are distributed between two amino acid chains: the A chain with 21 amino acids and the B chain with 30 amino acids. The chains are connected to one another by 2 disulfide bridges. Insulin compositions have been used for many years for the therapy of diabetes. This includes the use not only of naturally occurring insulins but also of insulin derivatives and analogs.

Insulin derivatives are derivatives of naturally occurring insulins, namely human insulin or animal insulins, which differ from the corresponding, otherwise identical naturally occurring insulin by substitution of at least one naturally occurring amino acid residue and/or addition of at least one amino acid residue and/or organic residue. It is understood that the term insulin defines a polypeptide composed out of a B- and A- chain. The insulin derivative may be at least 60% homologous to a naturally occurring insulin. The insulin derivative may be even more homologous, such as at least about 75%, or at least about 90%, homologous to a naturally occurring insulin. The % homology is calculated by the Compare Program, which is available from the WISCONSIN PACKAGE™ distributed by the Genetics Computer Group; 575 Science Drive; Madison, Wis.

In general, insulin derivatives have a slightly modified action compared with human insulin.

Insulin derivatives having an accelerated onset of action are described in EP 0 214 826, EP 0 375 437 and EP 0 678 522. Among other things, EP 0 124 826 relates to substitutions of B27 and B28. EP 0 678 522 describes insulin derivatives which have at position B29 various amino acids, such as proline, but not glutamic acid.

EP 0 375 437 discloses insulin derivatives with lysine or arginine at B28, which may additionally be modified at B3 and/or A21, where appropriate.

EP 0 419 504 discloses insulin derivatives which are protected against chemical modification by modification of asparagine at B3 and of at least one other amino acid at positions A5, A15, A18, and A21.

WO 92/00321 describes insulin derivatives in which at least one amino acid at positions B1–B6 has been replaced by lysine or arginine. According to WO 92/00321, insulins of this kind exhibit a prolonged action.

When producing insulin and insulin derivatives by genetic engineering, an insulin precursor, "proinsulin", comprising B, C and A chains is frequently expressed. Said proinsulin can be converted into insulin or an insulin derivative by enzymatic or chemical removal of the C chain after appropriate and correct folding and formation of the disulfides bridges. Proinsulin is frequently expressed in the form of a fusion protein. The "unwanted" fusion partner likewise needs be removed chemically or enzymatically. Proinsulin derivative may be at least 60% homologous in B- and A-chain of a naturally occurring proinsulin. The connecting C-peptide, however, may be chosen as being totally different from any known natural occurring C-peptide. The proinsulin derivative may be even more homologous, such as at least about 75%, or at least about 90%, homologous to a naturally occurring proinsulin. The % homology is calculated as described above.

The choice of recombinant host/vector systems determines the methods for cultivation, propagation and fermentation of the recombinant cells. This is likewise a subject of the invention.

The fusion protein shows surprisingly good solubility in acidic medium, and this leads to distinct advantages regarding the chemical workup of the protein. First, many unwanted components of the supernatant are precipitated under said conditions and, second, peptidases or proteases are inactive. Thus, acidifying the fermentation broth at the end of the operation makes it possible to directly separate unwanted supernatant proteins together with the host cells from the fusion protein and, in a further step, to concentrate said fusion protein. This is likewise a subject of the invention.

At the end of the fermentation, the folding process may not yet be 100% complete. The addition of mercaptan or, for example, cysteine hydrochloride can complete the process. This is likewise a subject of the invention.

If the two proteins are fused via a linker of amino acids that are specifically recognized by endoproteases which efficiently cleave the fusion protein at no other position, then the protein of interest can be cleaved off directly in active form. In the case of insulin production, the linker between hirudin and proinsulin may contain arginine at the carboxy-terminal end. In simultaneous processing it is then Possible by conversion with trypsin to cleave off the fusion part and convert proinsulin to mono- or di-Arg-insulin. Said linker must be optimized in relation to insulin processing such that cleaving off the hirudin part is not slower than cleavages in the C peptide sequence or a derivative thereof which links the B and A chains of insulin. This is likewise a subject of the invention. An example of an expression system which can be used is the vector pJF118, described in FIG. 1 of EP 0 468 539, which is incorporated by reference herein in its entirety. The vector is also published as pJF118EH by Fürste et al. (Gene 48, 119–131, 1986).

Plasmids containing DNA sequences encoding proinsulin or proinsulin derivatives are described, for example, in EP-A 0 489 780 and PCT/EP00/08537, which are incorporated by reference herein in their entireties.

The plasmid pK152 which contains the sequence for hirudin according to EP-A 0 324 712, which is incorporated by reference herein in its entirety, is used as source of the DNA sequence for hirudin.

The export compatibility of the protein of interest for passing through the inner bacterial membrane is important for secretion. In this context, the choice of signal sequence which can be more or less optimal for different proteins is important. The patent application PCT/EP00/08537 describes a system of PCR-based signal sequence screening. This system can also be applied to fusion proteins having hirudin as the N-terminal fusion part, since hirudin activity surprisingly remains intact and thus becomes readily detectable in the supernatant by means of the thrombin inhibition assay.

The invention therefore may relate to a DNA encoding a fusion protein of the form

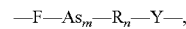

where
F is a DNA sequence coding for an amino acid sequence which allows secretion of a protein encoded by Y into a fermentation medium,
As is a chemical bond or a DNA sequence coding for an amino acid encodable by the genetic code,
m is an integer from 0–10,
R is a chemical bond or an arginine codon,
n is 0 or 1, and
Y is a DNA sequence coding for a protein of interest which, correctly folded, is part of the fusion protein in the fermentation medium.

For instance, the present invention may involve DNA sequences coding for hirudin or a derivative thereof (F) and proinsulin or a derivative thereof The invention further relates to an expression cassette (alternative term: DNA-molecule) of the form

where
P is a promoter,
S is a DNA sequence coding for a signal sequence allowing optimal yields,
T is an untranslated expression-enhancing DNA sequence.

The invention further may relate to a plasmid containing an above-described expression cassette and to a host cell containing said plasmid or to a host cell which may contain the expression cassette integrated into the host genome, the host cell being selected from *E. Coli, Bacillus subtilis,* and *Streptomyces lividans.*

The invention also may relate to a process for the fermentative production of a fusion protein as described above, in which process
(a) a DNA molecule as described above is expressed in a host cell as described above; and
(b) the expressed fusion protein is isolated.

For example, the supernatant may be separated from the host cells to isolate the expressed protein, and the expressed protein may be isolated from the supernatant; and in which a process step for concentrating the expressed protein in the supernatant after precipitation is selected from microfiltration, hydrophobic interaction chromatography and ion exchange chromatography, and in which a particular aspect is that isolation of the expressed protein includes a step in which components of the culture medium or the supernatant are precipitated, while the expressed protein remains in solution; and in which in a further preferred aspect of the invention, after the fermentation, mercaptan or cysteine hydrochloride are added to the fermentation supernatant at about pH 6 to 9, resulting in a free SH group concentration of from about 0.05 to 2.5 mM.

A particular aspect of the invention comprises separating the fermentation supernatant from the host cells, further culturing the host cells in fresh medium and isolating the released fusion protein from the supernatant. In other words, a further aspect of the invention is a process as described above, in which process after separating the fermentation supernatant from the host cells, the host cells are repeatedly cultured in fresh medium, and the released fusion protein is isolated from each supernatant obtained during cultivation.

The invention further relates to a process for the production of insulin or an insulin derivative, in which process
(a) from the expressed protein which is obtained in a process as described above,
(b) the protein of interest, in particular insulin or insulin derivative, is released by enzymatic or chemical cleavage, and
(c) is isolated.

Thus, in one aspect, the present invention is directed to a nucleic acid comprising a sequence coding for a fusion protein, the sequence comprising:

where
F is a nucleic acid sequence coding for an amino acid sequence which allows secretion of a protein encoded by Y into a fermentation medium,
As is a chemical bond or a nucleic acid sequence comprising a codon,
m is an integer from 0–10,
R is a chemical bond or an arginine codon,
n is 0 or 1, and
Y is a nucleic acid sequence coding for a protein of interest.

The nucleic acid may comprise:

where
P is a promoter,
S is a nucleic acid sequence coding for a signal sequence which increases yield, and
T is an untranslated expression-enhancing nucleic acid sequence.

The nucleic acid sequence S may be the oprF gene from *Pseudomonas fluorescens,* the nucleic acid encoding the signal sequence of *Salmonella typhimurium* outer membrane protein (fim D), the nucleic acid sequence encoding the signal sequence of the *Escherichia coli* alkaline phosphatase precursor protein, the nucleic acid sequence encoding the signal sequence smompa derived from the ompA gene for major outer membrane protein of *Serratia marcescens,* the nucleic acid sequence encoding the signal sequence ecoompc derived from *Escherichia coli* ompC gene coding for major outer membrane protein, the nucleic acid sequence encoding the signal sequence af009352 derived from *Bacillus subtilis* osmoprotectant binding protein precursor (opuCC), the nucleic acid sequence encoding the signal sequence aeoxyna derived from *Aeromonas caviae* xynA gene for xylanase I precursor, or the nucleic acid sequence encoding the signal sequence stomps1 derived from *Salmonella typhi* gene for outer membrane protein S1.

The nucleic acid sequence F may encode for lepirudin, Ser-hirudin or Ala-hirudin.

The protein of interest encoded by the nucleic acid may comprise proinsulin, insulin, or derivative thereof.

The protein of interest encoded by the nucleic acid may be correctly folded as part of the fusion protein in the fermentation medium.

In another aspect, the present invention is directed to a protein encoded by the nucleic acid.

In still another aspect, the present invention is directed to a plasmid comprising the nucleic acid.

In yet another aspect, the present invention is directed to a host cell comprising the nucleic acid or the plasmid. The host cell may be selected from *Escherichia coli, Bacillus subtilis,* and *Streptomyces lividans.* The nucleic acid may be integrated in the genome of the host cell.

In a further aspect, the present invention is directed to a process for fermentative production of a fusion protein, comprising: expressing the nucleic acid of the host cell to form the fusion protein; and isolating the fusion protein.

The isolating of the fusion protein may comprise separating the host cell from a supernatant containing the fusion protein, and isolating the fusion protein from the supernatant.

The isolating of the fusion protein may comprise precipitating the fusion protein from a supernatant containing the fusion protein and concentrating the fusion protein by one of microfiltration, hydrophobic interaction chromatography, and ion exchange chromatography.

The isolating of the fusion protein may comprise precipitating components of a culture medium or supernatant containing the fusion protein, while the fusion protein remains in solution.

The expressing of the nucleic acid in the host cell may comprise fermentation resulting in a fermentation supernatant, and wherein after the fermentation, mercaptan or cysteine hydrochloride is added to the fermentation supernatant at pH about 6 to 9, resulting in a free SH group concentration of about 0.05 to 2.5 mM.-

The expressing of the nucleic acid in the host cell may comprise fermentation resulting in a fermentation supernatant. The isolating of the fusion protein may comprise separating the fermentation supernatant from the host cell. After separating the fermentation supernatant from the host cell, the host cell may be repeatedly cultured in fresh medium to form additional supernatant from each culture, and fusion protein is isolated from each additional supernatant.

The expressing of the nucleic acid in the host cell may comprise forming a supernatant containing the fusion protein, and wherein mercaptan or cystein hydrochloride is added to the supernatant at pH about 6 to 9, so that the supernatant has a free SH group concentration of about 0.05 to 2.5 mM.

The isolating of the fusion protein may comprise isolating the fusion protein from a fermentation medium containing the fusion protein, and wherein the protein of interest is correctly folded as part of the fusion protein in the fermentation medium.

The host cell may comprise a bacterium.

In another aspect, the present invention is directed to a process for the production of insulin or an insulin derivative, comprising: obtaining fusion protein, releasing insulin or insulin derivative from the fusion protein by enzymatic or chemical cleavage, and isolating the insulin or insulin derivative.

The following examples which are not intended to be restrictive describe the invention in more detail.

EXAMPLE 1

Construction of a Lepirudin-GNSAR-simian Proinsulin Fusion Protein, Appended to the Signal Sequence of the oprF Gene Product from *Pseudomonas fluorescens*

Example 2 of the patent application PCT/EP00/08537, which is incorporated by reference herein in its entirety, describes an expression vector which allows expression and secretion of REFLUDAN™, into the medium used for *E. coli* via the signal sequence of the *Pseudomonas fluorescens* oprF gene product (De, E. et al., FEMS Microbiol Lett. 127, 263–272, 1995, which is incorporated by reference herein in its entirety. This vector served to construct a REFLUDAN™-GNSAR-simian proinsulin fusion protein (GNSAR=SEQ ID NO.: 1) and was denoted pBpfu_hir.

Further starting materials are pJF118 (EP 0 468 539, which is incorporated by reference herein in its entirety) and pK152 (PCT/EP00/08537, which is incorporated by reference herein in its entirety) plasmid DNAs. The following oligonucleotides were required:

```
Primer pfuf1
5'GGTTCTCTTA TTGCCGCTAC TTCTTTCGGC GTTCTGGCAc ttacgtatac tgactgca 3'  (SEQ ID NO.:2)
```

(the small letters in this sequence characterize the part of the sequence that matches to the hirudin (lepirudin) sequence)

Primer insu11hindIII

5'-TTTTT<u>AAGCTT</u> CATGTTTGA CAGCTTATCA-T-3' (SEQ ID NO.: 3)

(the underlining in this sequence is a restriction site for Hind3)

```
Primer Hir_insf1
5' ATCCCTGAGG AATACCTTCA GGGAAATTCG GCACGATTTG TG-3'  (SEQ ID NO.:4)

Primer Hir_insrev1
5'-CACAAATCGT GCCGAATTTC CCTGAAGGTA TTCCTCAGGG AT-3'  (SEQ ID NO.:5)
```

Primer pfuf1 hybridized with the DNA region encoding the junction of signal sequence and lepirudin in the expression vector.

The part of primer Hir_insrev1 shown in bold type hybridized with the DNA region encoding the junction of preproinsulin and simian proinsulin sequences in plasmid pINT90d (EP 489 780, which is incorporated by reference herein in its entirety) and with sequences of the 3'end of the hirudin sequence in plasmid pK152. Primer Hir_insrev1 was 100% complementary to primer Hir_insf1.

Primer Insu11HindIII marked the 3' end of the DNA region cloned in pINT90d and encoding the simian proinsulin sequence and additionally carried the hexanucleotide sequence for recognition by the restriction enzyme HindIII.

Two standard polymerase chain reactions were carried out using the Hir_insf1/Insu11HindIII primer pair with plasmid pINT90d as template and the pfuf1/Hir_insrev primer pair with plasmid pBpfu_hir as template. To perform the reactions the ADVANTAGE™-HF PCR Kit (Clontech Cat#K1909-1) was used. The reaction volume was 50 µl containing 1 µl polymerase, 5–10 ng template and about 100 ng of primer. 25 cycles: 30" at 95° C., 30" at 52° C. and 30" at 72° C. were run. The products of both reactions were isolated and about 5% of the yields were combined and converted in a third polymerase chain reaction which was run under the same conditions with primers pfuf1/Insu1 1HindIII. The result was a DNA product which contained the sequence signal (partially)-lepirudin-GNSAR-simian proinsulin. The DNA fragment was converted using restriction enzymes BamHI and HindIII (according to the manufacturer's protocol), with BamHI cleaving in the lepirudin sequence and HindIII at the 3' end of the proinsulin-encoding sequence.

In a parallel reaction, vector pBpfu was converted (according to the manufacturer's protocol) using the two enzymes and the large vector fragment was isolated. The isolated products of both reactions were converted in a T4 ligase reaction. Competent cells of the *E. coli* strain K12 Mc1061 (Sambrook et al. "Molecular Cloning" (Cold Spring Harbor Laboratory Press 1989), which is incorporated by reference herein in its entirety) were transformed with the ligation mixture and plated on NA plates containing 25 μg/ml ampicillin. Plasmid DNA was isolated from transformants for characterization. At the same time, a plate with the transformants characterized in the plasmid analysis was produced, by using the same technique, for maintenance purposes. The DNA was characterized by means of restriction analysis and DNA sequence analysis by standard techniques. A plasmid identified as correct was denoted pBpfu-Hir_Ins.

EXAMPLE 2

Construction of a Ser-Hirudin-GNSAR-simian Proinsulin Fusion Protein Appended to the Signal Sequence of *Salmonella typhimurium* Outer Membrane Protein (fimD)

As describe in more detail below, the construction was carried out similar to the plan described in Example 1.

Example 10 of PCT/EP 00/08537, which is incorporated by reference herein in its entirety, describes the construction of a vector for exporting lepirudin via the signal sequence of *Salmonella typhimurium* outer membrane protein (Rioux, C. R., Friedrich, M. J. and Kadner, R. J.;J. Bacteriol. 172 (11), 6217–6222 (1990), which is incorporated by reference herein in its entirety). The resulting plasmid was denoted pBstyfim_hir for laboratory purposes. DNAs of plasmids pK152 and pINT90d served in each case as templates.

The construction required 4 primers.

The primers insu1 1HindIII, Hir_insf1 and Hir_insrev1 are described in Example 1 of the present document.

The primer styfimf1ser was newly synthesized and had the following sequence:

5' CGGCGCTGAG TCTCGCCTTA TTTTCTCACC TATCTTTTGC CTCTacgtat actgactgcactg 3' (SEQ ID NO.:6)

(the small letters in this sequence characterize the part of the sequence that matches to the hirudin (lepirudin) sequence, and TCT is the codon for ser)

The DNA triplet shown in bold type indicates a serine codon. As a result, a hirudin was produced which carried serine instead of leucine at position 1 of the amino acid sequence.

Under the same conditions as Example 1, two standard polymerase chain reactions were carried out using the Hir_insf1/Insu1 1HindIII primer pair with pINT90d DNA as template and the styfimf1ser/Hir_insrev primer pair with pK152 DNA as template. As in Example 3 the products of both reactions were isolated and an aliquot of both yields was combined and was converted in a third polymerase chain reaction with primers styfim1ser Insu1 1HindIII. The result was a DNA product which contained the sequence signal Ser-hirudin-GNSAR-simian proinsulin. The DNA fragment was converted using the restriction enzymes BamHI and HindIII as described in Example 1.

In a parallel reaction, vector pBstyfim_Hir was converted using the two enzymes, BamHI and HindIII, and the large vector fragment was isolated. The isolated products of both reactions were converted in a T4-ligase reaction. Competent cells of *E. coli* strain K12 Mc1061 were transformed with the ligation mixture, and plasmid DNA was isolated from transformants for characterization. At the same time, a plate with the transformants characterized by plasmid analysis was produced for maintenance purposes. The DNA was characterized by means of restriction analysis and DNA sequence analysis by standard techniques. A plasmid identified as correct was denoted pBstyfim_SerHir_Ins.

EXAMPLE 3

Construction of an Ala-hirudin-R-simian Proinsulin Fusion Protein Appended to the Signal Sequence of the *E. coli* Alkaline Phosphatase Precursor Protein The *E. coli* alkaline phosphatase precursor had the signal sequence:

MKQSTIALAL LPLLFTPVTK A (SEQ ID NO.: 7)

(Shuttleworth, H., Taylor J., Minton N.; Nucleic Acids Res. 14:8689, (1986), which is incorporated by reference herein in its entirety).

The peptide sequence was translated into DNA by the GCG program Backtranslate (WISCONSIN PACKAGE™ Version 10.1, Genetics Computer Group (GCG), Madison, Wis.) using the *E. coli* high codon usage criteria.

This resulted in the sequence:

5'ATGAAACAGTCGACCATCGCGCTGGCGCTGCTGCCGCTGCTGTTCACCCCGGTTACCAAAGCG 3' (SEQ ID NO.:8)

To clone and append this sequence to a DNA sequence coding for a hirudin which was characterized by having the amino acid alanine at position 1 (EP-A 0 448 093, which is incorporated by reference herein in its entirety), said sequence was extended by the sequence shown in bold type:

5'TTTTTTGAATTCATGAAACAGTCGACCATCGCGCTGGCGCTGCTGCCGCTGCTGTTC (SEQ ID NO.:9)

ACCCCGGTTACCAAAG-CG GCTacgtat actgactgcactg

Ala

Two oligonucleotide sequences which partially overlap were derived therefrom.

Primer phoaf1 had the sequence:

5'CTGCTGCCGCTGCTGTTCACCCCGGTTACCAAAGCG GCTACGTATACTGACTGCACTG-3' (SEQ ID NO.:10)

Primer phoaf2 had the sequence:

5'-TTTTTTGAATTCATGAAACAGTCGACCATCGCGCTGGCGCTGCTGCCGCTGCTG-3' (SEQ ID NO.:11)

The construction of the expression vector required primers insu11HindIII, Hir_insf2 and Hir_insrev2 and DNAs of plasmids pK152, pINT90d and pJF118.

Primer Hir_insf2 had the sequence:

5'-ATCCCTGAGGAATACCTTCAG<u>cga</u>TTTGTGAACCAGCAC C-3' (SEQ ID NO.12)

Primer Hir_insrev2 had the sequence:

5'-GGTGCTGGTTCACAAA<u>tcg</u>CTGAAGGTA TTCCTCAGGG AT-3' (SEQ ID NO.13)

Upper case letters in bold type indicate the sequence hybridizing with proinsulin, while upper case letters in plain type describe overlap with the 3' end of the hirudin sequence. Lower case letters underlined and in bold type represent the codon for the linker arginine.

Under the same conditions as Example 1, two standard polymerase chain reactions were carried out using the Hir_insf1/Insu11HindIII primer pair with pINT90d DNA as template and the phoaf1/Hir_insrev primer pair with pK 152 DNA as template. In the same manner as Example 1, the products of both reactions were combined and an aliquot was converted in a third polymerase chain reaction with primers phoa/Insu1 1HindIII. The result was a DNA product which contains the sequence signal-Ala-hirudin-GNSAR-simian proinsulin. Under the same conditions as Example 1, the DNA fragment was converted using restriction enzymes BamHI and HindIII. In a parallel reaction, vector pjF118 was converted using the two enzymes, BamHI and HindIII, and the large vector fragment was isolated in accordance with Example 1. The isolated products of both reactions were converted in a T4-ligase reaction. Competent cells of E. coli strain K12 Mc1061 were transformed with the ligation mixture, and plasmid DNA was isolated from transformants for characterization. At the same time, a plate with the transformants characterized by plasmid analysis was produced for maintenance purposes. The DNA was characterized by means of restriction analysis and DNA sequence analysis by standard techniques. A plasmid identified as correct was denoted pNS22.

EXAMPLE 4

Thrombin Inhibition Assay

The hirudin concentration of the supernatant of Example 5 was determined according to the method of Grießbach et al. (Thrombosis Research 37, pp. 347–350 1985, which is incorporated by reference herein in its entirety). For this purpose, REFLUDAN™ standard was included in the measurements in order to establish a calibration curve from which the yield in mg/l was determined directly. The biological activity (unfolded molecules are not active) was also a direct measure for correct folding of the proinsulin component of the fusion protein. Alternatively, although not conducted as part of this Example, it is possible to use a proteolytic Staphylococcus aureus digestion and subsequent analysis in an RP-HPLC system in order to perform a peptide mapping to determine the correct S—S bridge formation.

EXAMPLE 5

Expression of the Fusion Protein

Recombinant cells were cultivated overnight in an incubation shaker at 30° C. and 220 rpm in 2YT medium (per liter: 16 g of tryptone, 10 g of yeast extract, 5 g of NaCl) containing 100 μg/ml ampicillin. The overnight culture was diluted 1:50 with fresh medium and the cells were grown in an incubation shaker at 30° C. and 220 rpm to a density of approximately 0.8 $OD_{600}$.

Expression was then induced by adding IPTG in such a way that a concentration of 0.05–2 mM was established. The cells induced in this way were incubated under the same conditions as described above for a further 3–26 h.

After three hours, an antithrombin action of hirudin was clearly measurable in the supernatant by the method of Example 4 of this document. Said action was attributed to secretion of the desired fusion protein, since SDS PAGE analysis, after Coomassie blue staining, revealed only in induced cells a new band which reacted in Western blot analysis with polyclonal anti-insulin antibodies. In fermentation experiments, induction was commenced only after cultivation to significantly higher (10 to 20) optical densities. Preference was given here to synthetic media based on minimal medium.

Cell productivity was increased by using the principle of bacterial milking, i.e., by carefully removing the cells by centrifugation or filtration, after the optimal induction time which was dependent on the equipment used, from the supernatant and further incubating them under the same conditions as described above in fresh synthetic medium to which the inducer IPTG was again added. Insulin was then prepared, as described in Examples 6–8, in parallel from the harvested supernatant.

EXAMPLE 6

Purification of the Fusion Protein

After induction was finished, the cell supernatant was adjusted to pH 2.5–3 and cells and supernatant components were removed by centrifugation or filtration. The supernatant of the precipitation was applied to a cation exchange column (S-Hyper DF, Source 30S) and fractionated using a linear gradient from 150 to 450 mM NaCl at pH 3.5 in the presence of 30% (v/v) 2-propanol. The individual fractions were analyzed by means of RP-HPLC. The proinsulin-hirudin fusion protein was eluted at an NaCl concentration of about 300 mM. Sufficiently pure fractions were combined, diluted with 0.1% (v/v) TFA and applied to an RP column (PLRP-S 7.5×50 mm) by pumping. Elution was carried out using a gradient of 25–50% acetonitrile. Two groups of fractions were pooled. After removing the solvent, the material was freeze-dried. The purity of the material was checked by means of SDS polyacrylamide electrophoresis. The purified fusion protein was analyzed by mass spectrometry (ESI). The experimentally determined molecular weight of the fusion protein corresponded to its theoretically expected molecular weight after removal of the signal peptide.

EXAMPLE 7

Determination of the Disulfide Bridge Linkage

The fusion protein was digested with trypsin, as described below, and the fragments formed were analyzed by means of RP-HPLC and subsequently by means of mass spectrometry. A fragment which was recognized as de-(B30) insulin, due to its mass of 5706 Da, was successfully identified. This product was subjected to S. aureus V8 protease digestion as described below. RP-HPLC analysis showed the expected peptide pattern.

Trypsin cleavage was carried out as follows:

The freeze-dried fusion protein was dissolved in 50 mMTris-HCl pH 8 (1 mg/ml), and trypsin (1 μg per mg of fusion protein) was added. Trypsin was inactivated at pH 3 at the end of the reaction.

The S. aureus digestion was carried out as follows:

The isolated de-(B30) insulin was dissolved in water at pH 8, S. aureus protease (1/50 of the amount of insulin) was added, and the mixture was incubated at 37° C. for 5 hours and then at room temperature overnight.

EXAMPLE 8

Purification of Insulin

In contrast to most other polypeptides found in the supernatant due to either spontaneous lysis of host cells or secretion, the fusion protein is surprisingly not precipitated at pH 2.5–3.5. The culture medium is therefore acidified with concentrated HCl appropriately to pH 2.5–3.5 and then, after completion of the precipitation, the precipitate and the cells are removed by centrifugation at 3000 to 10000×g or by microfiltration and concentrated.

Subsequently, the medium is adjusted with concentrated NaOH to pH 6.8 and the fusion protein content is determined in parallel by analytical HPLC measurement. The determination is followed by adding trypsin to the supernatant so that trypsin is at approximately 1 μg per 1–1.5 mg of fusion protein. After incubation at room temperature for approx. 4 hours, purification is carried out by cation exchange chromatography using a S-Hyperfine DF or Source-30S column at pH 3.5 in the presence of 2-propanol. Elution is carried out in the buffer by applying a linear gradient of from 0.15 to 0.45 M NaCl.

Di-Arg-insulin is eluted at approximately 0.3 M NaCl. After 1:1 dilution with $H_2O$, di-Arg-insulin is precipitated from the insulin-containing fractions at pH 6.8 with the addition of a 10% strength $ZnCl_2$ solution until the protein precipitates at 0.1% $ZnCl_2$. Insulin is filtered off and then dissolved in 0.05 M Tris-HCl (pH 8.5) resulting in a 2 mg/ml solution:

Then, the amount of approximately 1 unit of carboxypeptidase B per 100 ml solution is added and the reaction is carried out with gentle stirring. The pH is then adjusted to pH 5.5 with citric acid, and insulin is crystallized in the presence of $ZnCl_2$. The crystals are removed, dissolved and, after purification by RP-HPLC, insulin is purified again by crystallization.

EXAMPLE 9

Processing of the Fusion Protein Directly in the Culture Medium

At the end of the expression period, the culture medium is adjusted to pH 6.8 and trypsin is then added with stirring so that a final concentration of 4–8 mg per liter is established. After incubation for approximately 4 hours, the fermentation broth treated in this way is adjusted to pH 2.5–3. After 1–6 hours of precipitation, the pH is raised to 3.5, and the di-Arg-insulin formed is purified via cation exchange chromatography using a Source-30S cation exchange column in the presence of 30% (v/v) 2-propanol. Elution is carried out by means of a linear NaCl gradient of 0.05–0.5 M salt. The product-containing fractions are diluted 1:1 with $H_2O$ and then $ZnCl_2$ is added, so that a 0.1% strength $ZnCl_2$ solution is formed. Di-Arg-insulin precipitates at pH 6.8 and by way of example is converted to insulin according to Example 8.

EXAMPLE 10

Further Signal Sequences for the Secretion of Fusion Proteins

Using the technique described by PCT/EP00/08537, which is incorporated by reference in its entirety, further signal sequences leading to the secretion of hirudin—proinsulin fusion protein was detected:

Signal sequence smompa derived from the ompA gene for major outer membrane protein of Serratia marcescens (GenEMBL data base locus: SMOMPA, 1364 bp DNA BCT 30 Mar. 1995)

Signal sequence ecoompc derived from *E. coli* ompC gene coding for major outer membrane protein.

Signal sequence af009352 derived from *Bacillus subtilis* osmoprotectant binding protein precursor (opuCC) (GenEMBL data base locus: AF009352, 4500 bp, DNA BCT 23 Jul. 1997)

Signal sequence aeoxyna derived from *Aeromonas caviae* xynA gene for xylanase I precursor (GenEMBL data base locus: AEOXYNA, 1139 bp, DNA BCT 7 Feb. 1999)

Signal sequence stomps1 derived from *Salmonella typhi* gene for outer membrane protein S1 (GenEMBL data base locus: STOMPS1, 1938 bp, DNA BCT 24 Aug. 1995)

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A nucleic acid comprising a sequence coding for a fusion protein, the sequence comprising:

-Hir-As$_m$—R$_n$—Y— where
wherein Hir is hirudin,
As is a nucleic acid sequence comprising a codon,
m is an integer from 0–10,
R is an arginine codon,
n is 0 or 1, and
Y is a nucleic acid sequence coding for proinsulin or insulin.

2. The nucleic acid of claim 1, wherein the nucleic acid comprises:

——P—S-Hir-As$_m$—R$_n$—Y—T— where
P is a promoter,
S is a nucleic acid sequence coding for a signal sequence which increases yield,
T is an untranslated expression-enhancing DNA sequence, and
wherein Hir, As$_m$, R$_n$, and Y are as defined in claim 1.

3. The nucleic acid of claim 2, wherein S is the oprF gene from *Pseudomonas fluorescens*, the nucleic acid encoding the signal sequence of *Salmonella typhimurium* outer membrane protein (fim D), the nucleic acid sequence encoding the signal sequence of the *Escherichia coli* alkaline phosphatase precursor protein, the nucleic acid sequence encoding the signal sequence smompa of the ompA gene for major outer membrane protein of *Serratia marcescens*, the nucleic acid sequence encoding the signal sequence ecoompe of *Escherichia coli* ompC gene coding for major outer membrane protein, the nucleic acid sequence encoding the signal sequence af009352 of *Bacillus subtilis* osmoprotectant binding protein precursor (opuCC), the nucleic acid sequence encoding the signal sequence aeoxyna of *Aeromonas caviae* xynA gene for xylanase I precursor, or the nucleic acid sequence encoding the signal sequence of stomps1 of *Salmonella typhi* gene for outer membrane protein S1.

4. The nucleic acid of claim 2, wherein the nucleic acid sequence Hir encodes for lepirudin, Val-Val-hirudin, Ile-Thr-hirudin, Ser-hirudin or Ala-hirudin.

5. The nucleic acid of claim 4, wherein nucleic acid sequence Hir encodes for lepirudin, Ser-hirudin or Ala-hirudin.

6. A plasmid comprising the nucleic acid of claim 1.

7. A host cell comprising the plasmid of claim 6.

8. A host cell comprising the nucleic acid of claim 2.

9. The host cell of claim 7, wherein the host cell is selected from *Escherichia coli, Bacillus subtilis*, and *Streptomyces lividans*.

10. The host cell of claim 8, wherein the host cell is selected from *Escherichia coli, Bacillus subtilis*, and *Streptomyces lividans*, and wherein the nucleic acid is optionally integrated in the genome of the host cell.

11. A process for fermentative production of a fusion protein, comprising: fermenting the host cell of claim 8, in a fermentation medium resulting in a fermentation supernatant and isolating the fusion protein produced by the host cell of claim 8.

12. The process of claim 11, wherein isolating the fusion protein comprises precipitating the fusion protein from the supernatant and concentrating the fusion protein by one of microfiltration, hydrophobic interaction chromatography, and ion exchange chromatography.

13. The process of claim 11, wherein isolating the fusion protein comprises precipitating components of the fermentation medium or the supernatant, while the fusion protein remains in solution.

14. The process of claim 11, wherein after the fermentation, mercaptan or cysteine hydrochloride is added to the fermentation supernatant at pH about 6 to 9, resulting in a free SH group concentration of about 0.05 to 2.5 mM.

15. The process of claim 11, wherein: isolating the fusion protein comprises separating the fermentation supernatant from the host cell, and after separating the fermentation supernatant from the host cell, the host cell is repeatedly cultured in fresh medium to form additional supernatant from each culture, and fusion protein is isolated from each additional supernatant.

16. The process of claim 11, wherein: mercaptan or cysteine hydrochloride is added to the supernatant at pH about 6 to 9, so that the supernatant has a free SH group concentration of about 0.05 to 2.5 mM.

17. A process for the production of insulin, comprising:
obtaining fusion protein by fermenting a host cell comprising the nucleic acid of claim 5 in a fermentation medium and isolating the fusion protein produced by the host cell,
releasing insulin from the fusion protein by enzymatic or chemical cleavage; and
isolating the insulin.

18. The process of claim 11, wherein the host cell comprises a bacterium.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:pBpfu_hir

<400> SEQUENCE: 1

Gly Asn Ser Ala Arg
 1               5

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence:pfuf1

<400> SEQUENCE: 2
ggttctctta ttgccgctac ttctttcggc gttctggcac ttacgtatac tgactgca         58

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:insu11hindl11

<400> SEQUENCE: 3
tttttaagct tcatgtttga cagcttatca t                                      31

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:Hir_insf1

<400> SEQUENCE: 4
atccctgagg aataccttca gggaaattcg gcacgatttg tg                          42

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:Hir_insrev1

<400> SEQUENCE: 5
```
cacaaatcgt gccgaatttc cctgaaggta ttcctcaggg at                           42

<210> SEQ ID NO 6
<211> LENGTH: 63
<212> TYPE: DNA
<213> ORGANISM: Artificial Sequence
<220> FEATURE:
<223> OTHER INFORMATION: Description of Artificial Sequence:styfimf1

<400> SEQUENCE: 6
cggcgctgag tctcgcctta ttttctcacc tatcttttgc ctctacgtat actgactgca      60
ctg                                                                    63

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: alkaline
      phosphatase (signal sequence)

<400> SEQUENCE: 7

Met Lys Gln Ser Thr Ile Ala Leu Ala Leu Leu Pro Leu Leu Phe Thr
 1               5                  10                  15

Pro Val Thr Lys Ala
            20

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence:alkaline
      phosphatase (signal sequence)

<400> SEQUENCE: 8
atgaaacagt cgaccatcgc gctggcgctg ctgccgctgc tgttcacccc ggttaccaaa      60
gcg                                                                    63

<210> SEQ ID NO 9
<211> LENGTH: 97
<212> TYPE: DNA
<213> ORGANISM: Artificial Sequence
<220> FEATURE:
<223> OTHER INFORMATION: Description of Artificial Sequence:cloning
      fragment

<400> SEQUENCE: 9 tttttttgaat tcatgaaaca gtcgaccatc gcgctggcgc tgctgccgct gctgttcacc      60
ccggttacca aagcggctac gtatactgac tgcactg                               97

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence:phoaf1

<400> SEQUENCE: 10
ctgctgccgc tgctgttcac cccggttacc aaagcggcta cgtatactga ctgcactg       58

<210> SEQ ID NO 11
<211> LENGTH: 54
<212> TYPE: DNA

```
<213> ORGANISM: Artificial Sequence
<220> FEATURE:
<223> OTHER INFORMATION: Description of Artificial Sequence:phoaf2

<400> SEQUENCE: 11 tttttttgaat tcatgaaaca gtcgaccatc gcgctggcgc tgctgccgct gctg            54

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:Hir_insf2

<400> SEQUENCE: 12
atccctgagg aataccttca gcgatttgtg aaccagcacc                             40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:Hir_insrev2

<400> SEQUENCE: 13
ggtgctggtt cacaaatcgc tgaaggtatt cctcagggat                             40
```